United States Patent [19]

Yukawa et al.

[11] Patent Number: 5,504,959
[45] Date of Patent: Apr. 9, 1996

[54] ELECTRIC TOOTHBRUSH

[75] Inventors: Kazuhiko Yukawa; Yoji Kawamoto, both of Hikone, Japan

[73] Assignee: Matsushita Electric Works, Ltd., Osaka, Japan

[21] Appl. No.: 256,153

[22] PCT Filed: Mar. 24, 1994

[86] PCT No.: PCT/JP94/00468

§ 371 Date: Jul. 8, 1994

§ 102(e) Date: Jul. 8, 1994

[51] Int. Cl.⁶ .............................. A61C 17/22; A46B 13/02
[52] U.S. Cl. .............................. 15/22.1; 15/22.2; 15/22.4; 15/28
[58] Field of Search ........................ 15/22.1, 22.2, 15/22.4, 28

[56] References Cited

U.S. PATENT DOCUMENTS

| | | | |
|---|---|---|---|
| 2,095,956 | 10/1937 | Bess | 15/22.2 |
| 4,156,620 | 5/1979 | Clemens . | |
| 4,989,287 | 2/1991 | Scherer | 15/22.1 |
| 5,253,382 | 10/1993 | Beny | 15/22.2 |
| 5,321,866 | 6/1994 | Klupt | 15/22.1 |
| 5,383,242 | 1/1995 | Bigler et al. | 15/22.1 |

FOREIGN PATENT DOCUMENTS

| | | | |
|---|---|---|---|
| 2578408 | 9/1986 | France | 15/22.1 |
| 2838015 | 3/1979 | Germany | 15/22.1 |
| 3526480 | 2/1987 | Germany | 15/22.1 |
| 54-33148 | 3/1979 | Japan . | |
| 61-156526 | 1/1986 | Japan . | |
| 63-77404 | 4/1988 | Japan . | |
| 2-114908 | 4/1990 | Japan . | |
| 4-15426 | 2/1992 | Japan . | |
| 5-137616 | 6/1993 | Japan | 15/22.1 |
| 5-146313 | 6/1993 | Japan | 15/22.2 |
| 5-207913 | 8/1993 | Japan | 15/22.1 |
| 5-199917 | 8/1993 | Japan | 15/22.2 |
| 5-199918 | 8/1993 | Japan | 15/22.1 |

*Primary Examiner*—Mark Spisich
*Attorney, Agent, or Firm*—Stevens, Davis, Miller & Mosher

[57] ABSTRACT

A brush provided on an end surface of a handle is equipped with a drive device capable of producing a reciprocating rectilinear motion in the direction of a handle axis and a reciprocating motion about the handle axis, while also producing a reciprocating motion about an axis in the direction of brush projection. The brush moves in a combination of the reciprocating rectilinear motion in the direction of the handle axis, the reciprocating motion about the handle axis, and the reciprocating motion about the axis in the direction of brush projection, and therefore scrub area increases, by virtue of the motion of the brush, the brush does not become trapped between teeth, and cleaning of the entire tooth surface is possible.

7 Claims, 17 Drawing Sheets

16 32 16 32                                    16 32

5,504,959

1

ELECTRIC TOOTHBRUSH

TECHNICAL FIELD

The invention concerns an electric toothbrush in which a toothbrush is electrically driven.

BACKGROUND ART

A toothbrush is composed of a brush projecting from one side of the end of a handle. Electric toothbrushes, in which the toothbrush is electrically driven, are available in a bus-brushing type where the toothbrush moves in a reciprocating rectilinear fashion in the direction of the axis of its handle, and in a rolling-brushing type where the toothbrush moves in a reciprocating fashion about the axis of its handle.

With the bus-brushing type, however, the brush of the toothbrush can get trapped between teeth, particularly between molars, so that the stroke becomes small and reduces scrubbing effectiveness. With the rolling-brushing type, there is a risk of gums being folded back or of injury being inflicted to the gums.

Another electric toothbrush is available in which a brush is mounted on a rotating base and moves in a reciprocating fashion about an axis in the direction of brush projection, but since this device requires that the brush be placed against each individual tooth, brushing of teeth takes an extremely long time.

DISCLOSURE OF THE INVENTION

The present invention was made in light of issues such as these, and the object of the invention lies in the provision of an electric toothbrush that permits effective brushing of teeth while retaining a large scrub area.

The invention also has a characteristic wherein a brush arranged on the end surface of a handle is equipped with a driving device capable of producing a reciprocating rectilinear motion in the direction of the handle axis and a reciprocating motion about the handle axis, while simultaneously producing a reciprocating motion about an axis in the direction of brush projection.

According to the invention, the brush moves in a combination of the reciprocating rectilinear motion in the direction of the handle axis, the reciprocating motion about the handle axis, and the reciprocating motion about the axis in the direction of brush projection, and therefore scrub area increases, by virtue of the fact that the motion the brush does not become trapped between teeth, and cleaning of the entire tooth surface is possible.

2

Figure 7A:
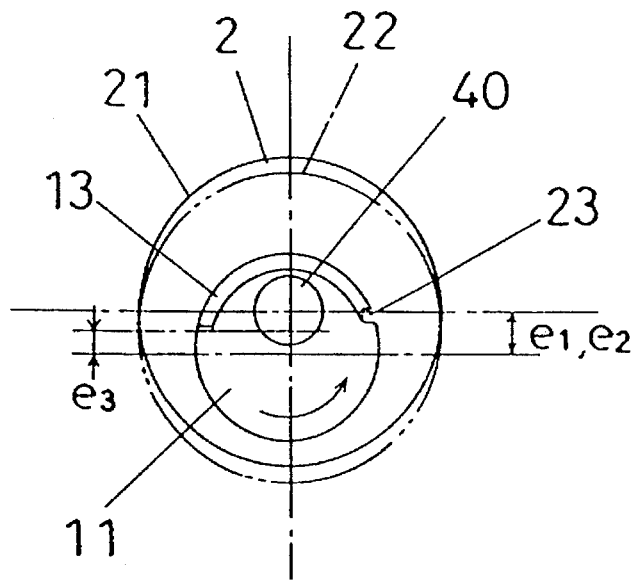
Figure 7B:
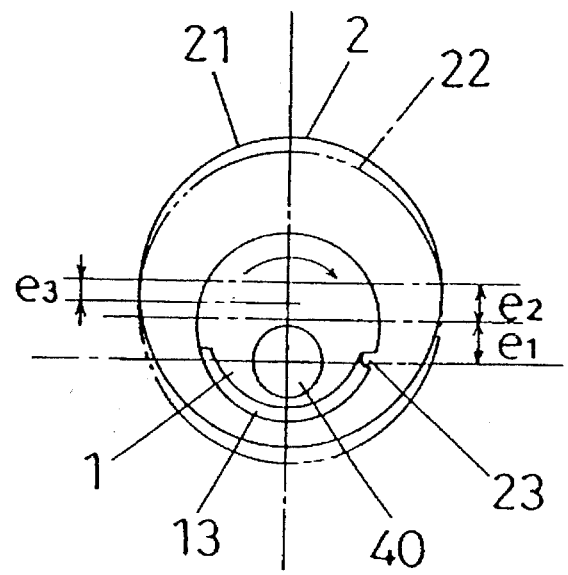
Figure 8A:
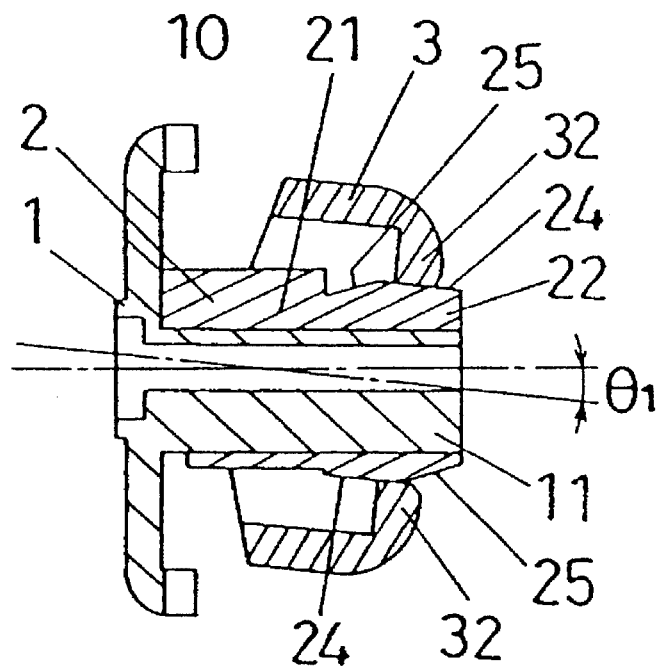
Figure 8B:
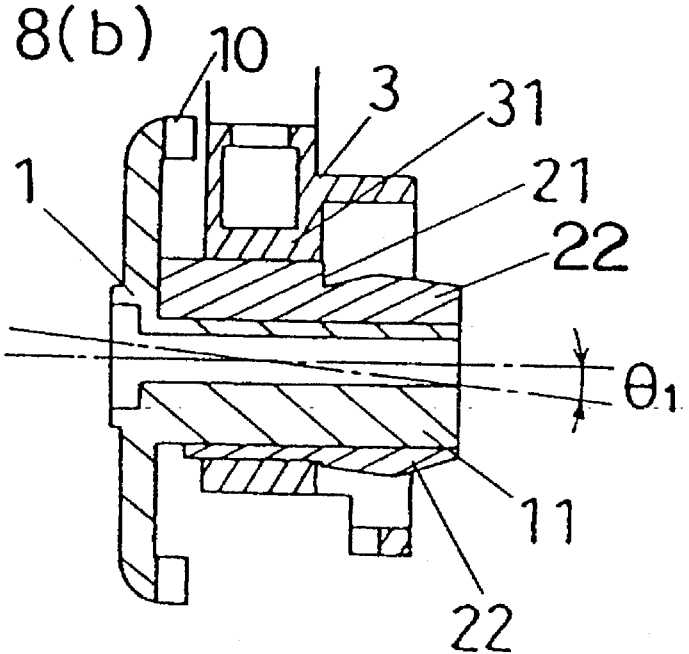
Figure 9A:
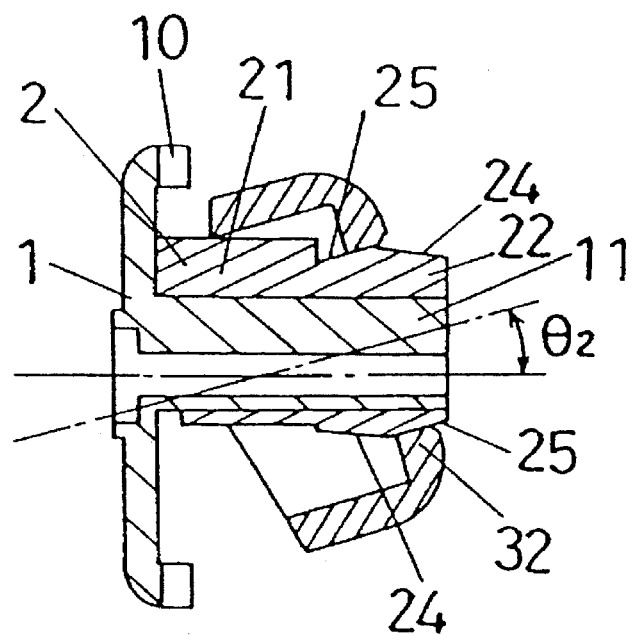
Figure 9B:
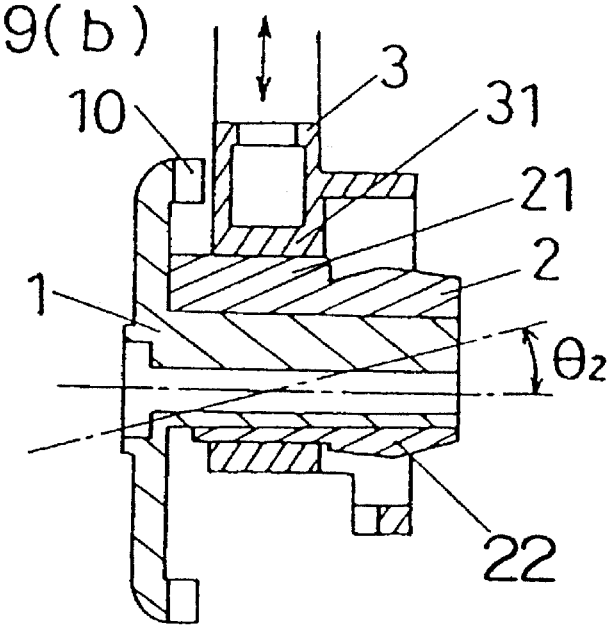
Figure 10A:
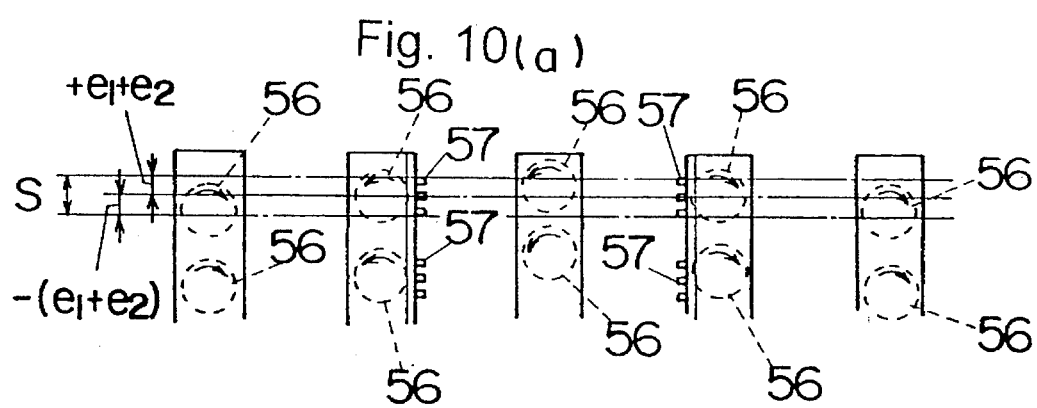
Figure 10B:
Figure 11:
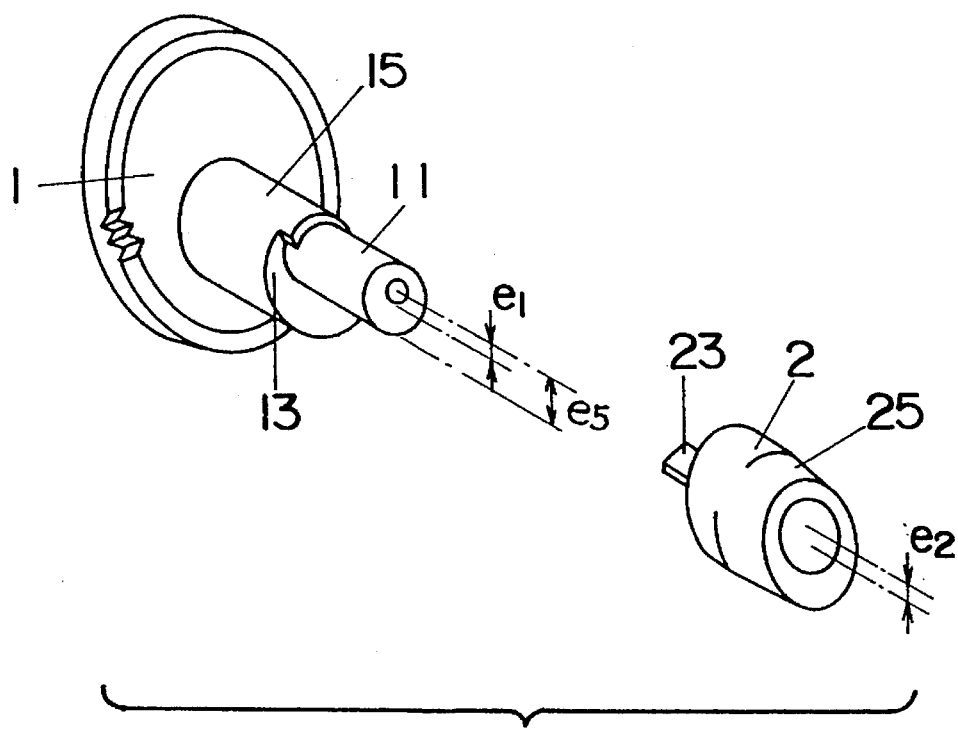
Figure 12A:
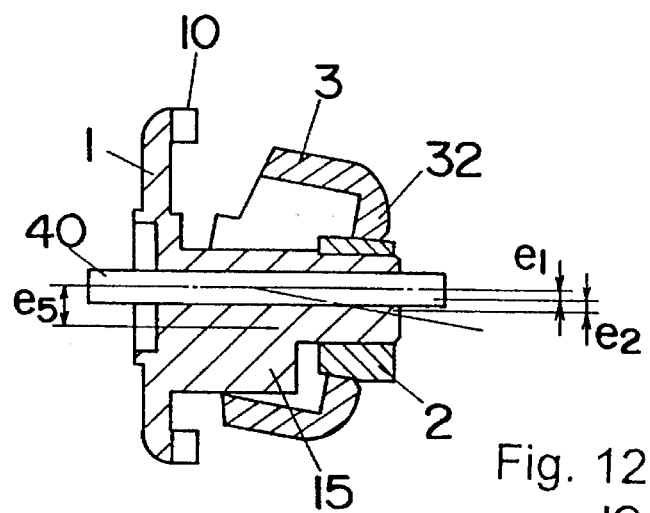
Figure 12B:
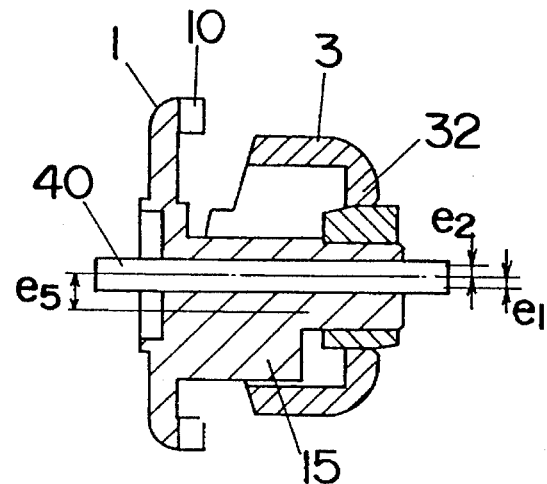
Figure 12C:
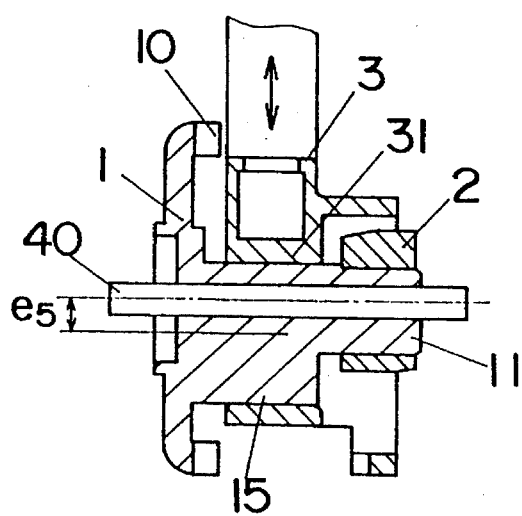
Figure 13:
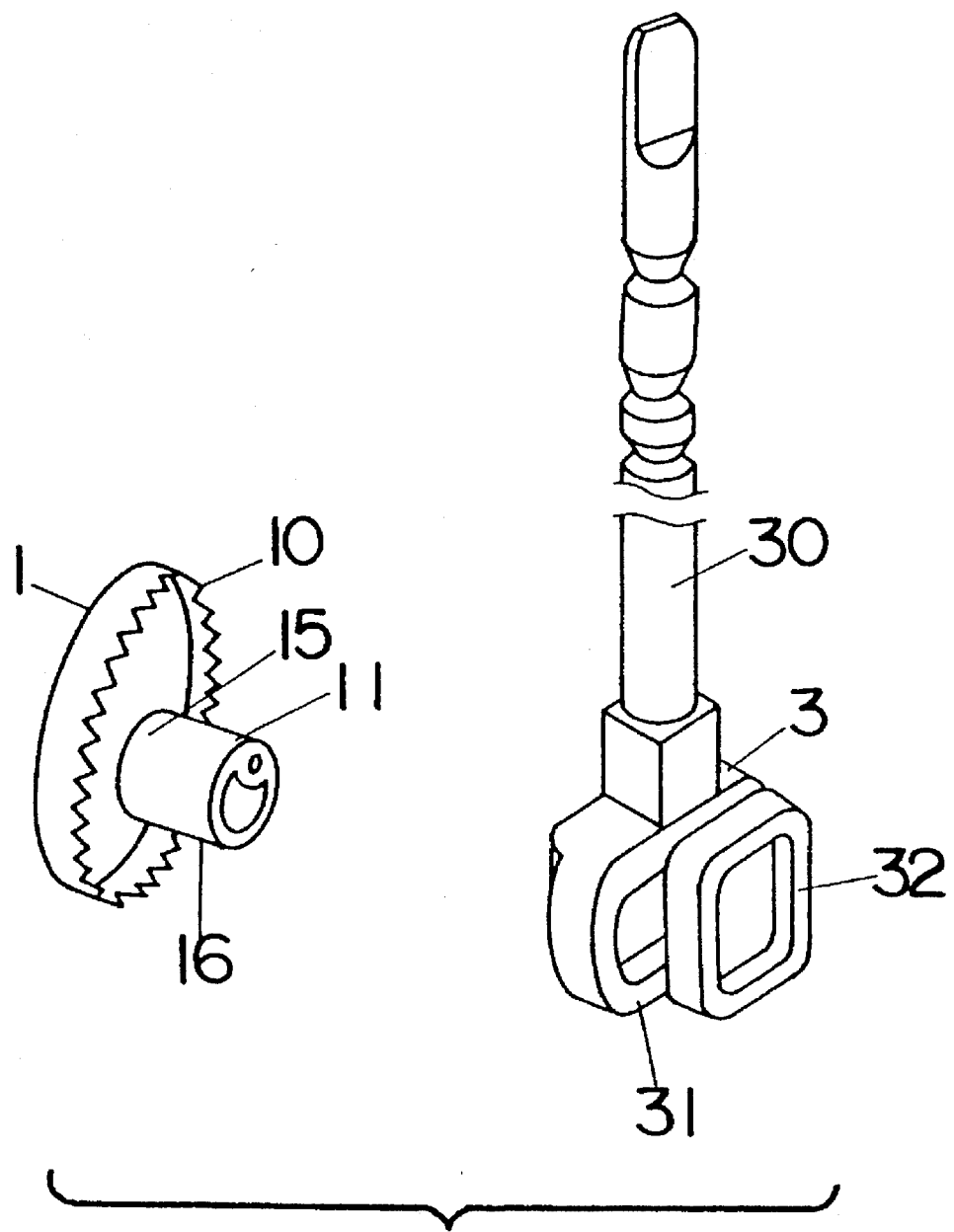
Figure 14A:
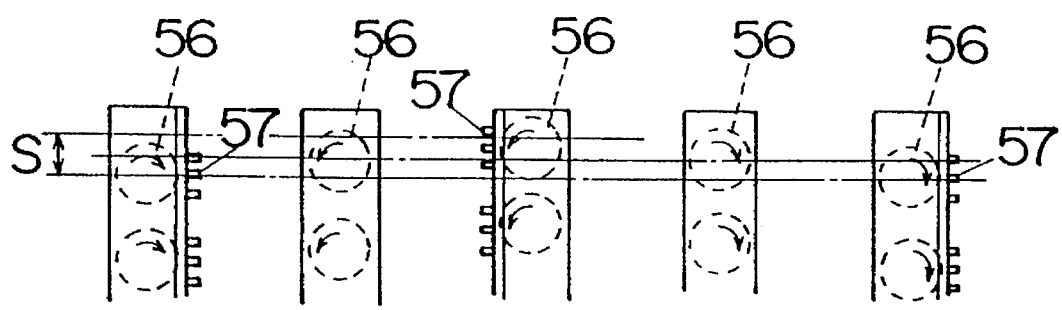
Figure 14B:
Figure 15:
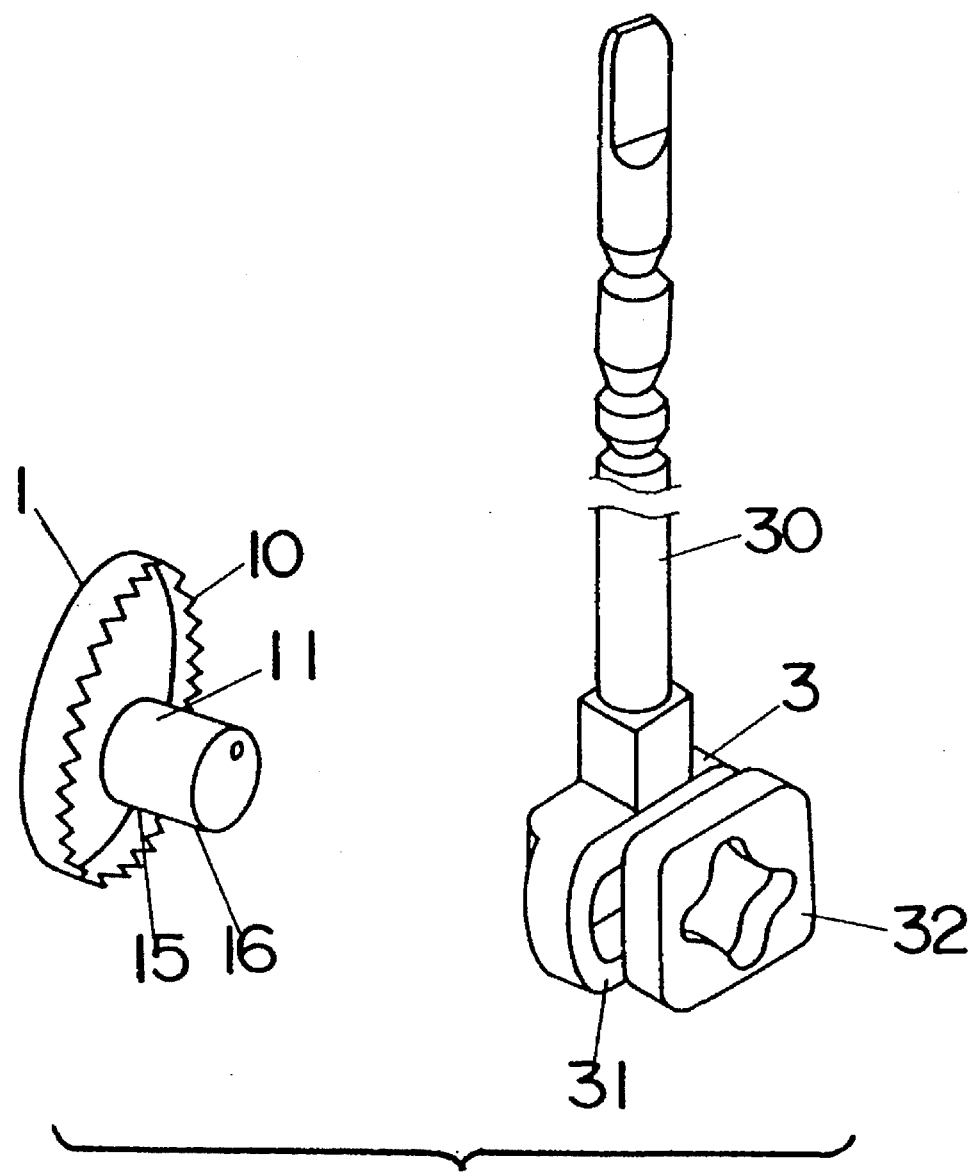
Figure 16A:
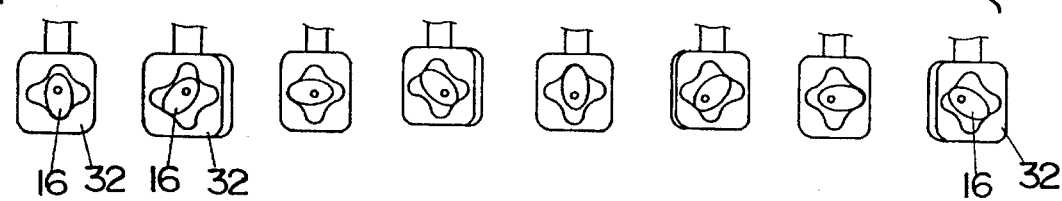
Figure 16B:

FIGS. 7(a) and 7(b) are front views illustrating eccentricities in the cam block;

FIGS. 8(a) and 8(b) illustrate one action of the cam block, wherein FIG. 8(a) is a horizontal cross-sectional diagram, and FIG. 8(b) is a vertical cross-sectional diagram;

FIGS. 9(a) and 9(b) illustrate another action of the cam block, wherein FIG. 9(a) is a horizontal cross-sectional diagram, and FIG. 9(b) is a vertical cross-sectional diagram;

FIGS. 10(a) and 10(b) illustrate an action of a brush of the toothbrush;

FIG. 11 is a perspective exploded view of a cam block of another exemplary embodiment of the invention;

FIGS. 12(a) to 12(c) depict actions of the cam block of FIG. 11, wherein FIG. 12(a) is a horizontal cross-sectional diagram showing a rotation in one direction, and FIGS. 12(b) and 12(c) are a horizontal cross-sectional diagram and vertical cross-sectional diagram showing a rotation in the other direction;

FIG. 13 is an oblique exploded view of a cam block of still another embodiment of the invention;

FIGS. 14(a) and 14(b) illustrate an action of a brush of a toothbrush when the cam block of FIG. 13 is used;

FIG. 15 is a perspective exploded view of a cam block of still another embodiment of the invention;

FIGS. 16(a) and 16(b) illustrate an action of the cam block of FIG. 15; and

Figure 17:
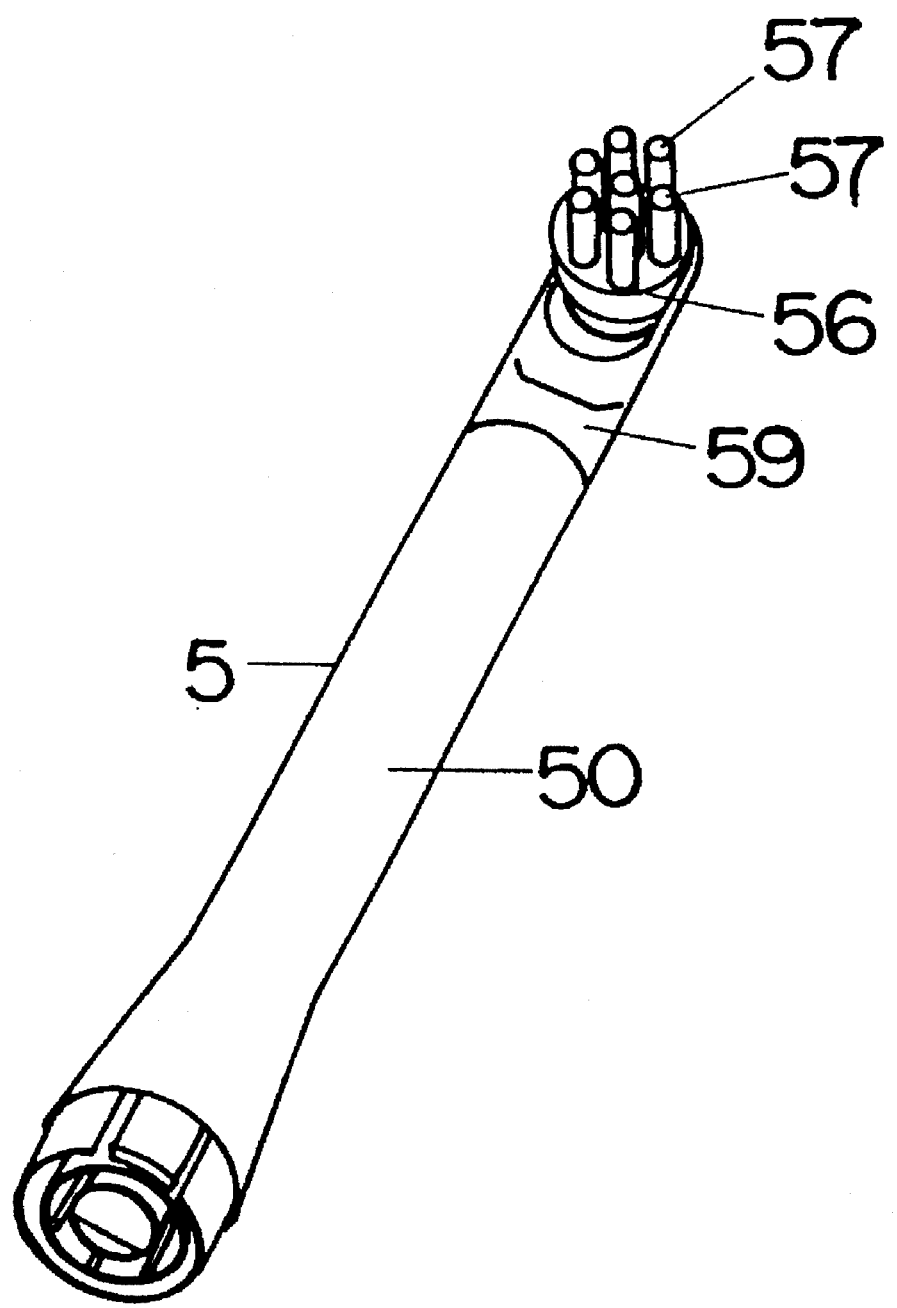

FIG. 17 is a perspective view of a toothbrush attachment of another embodiment of the invention.

BEST MODE FOR CARRYING OUT THE INVENTION

The invention is described by means of exemplary embodiments depicted in the drawings.

Figure 1:
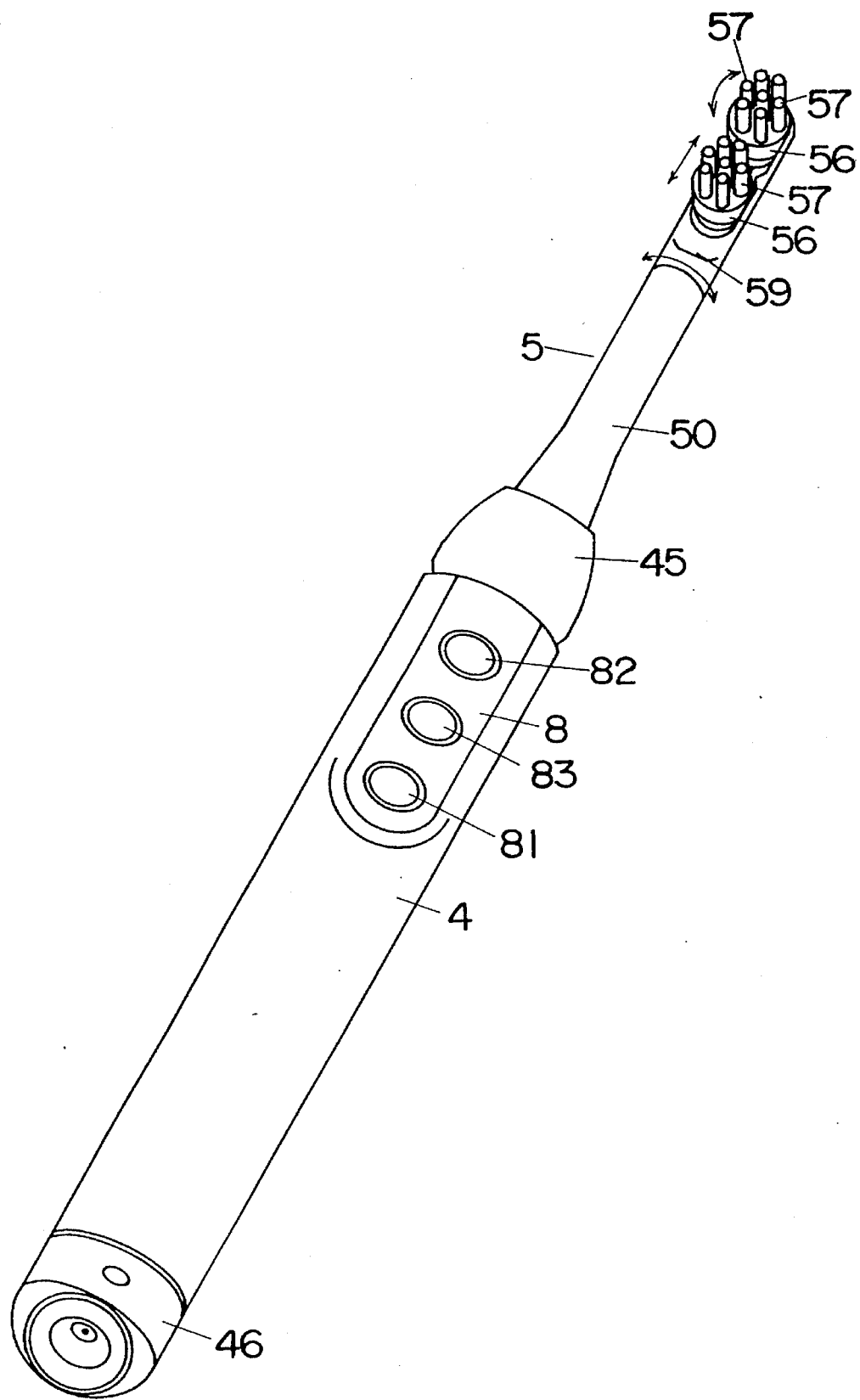
FIG. 1 is a perspective view of an electric toothbrush of an exemplary embodiment of the invention.
Figure 2:
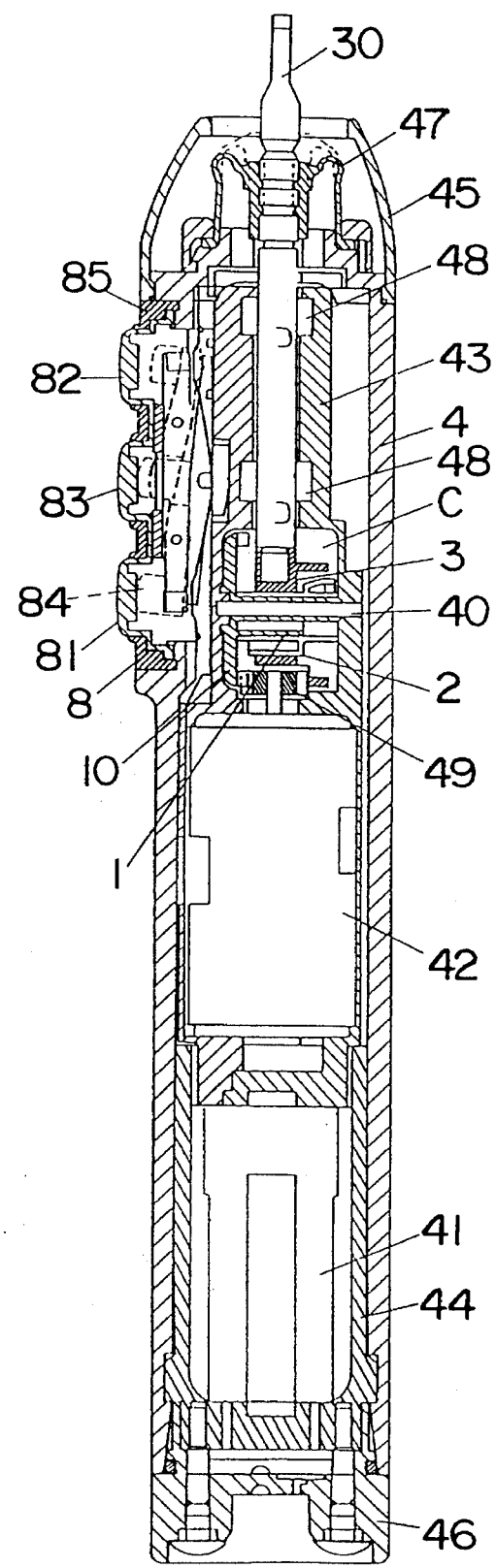
FIG. 2 is a cross-sectional diagram of the electric toothbrush.

An electric toothbrush depicted in the figures includes a long cylindrical housing 4, which contains a storage battery 41, a motor 42, and the like, and a toothbrush attachment 5, which is connected to a drive shaft 30 projecting from one end of the housing 4. As shown in FIG. 2, a frame 43 mounting the motor 42 and a cam block C therein, and a battery holder 44 mounting a storage battery 41 therein, are incorporated within the housing 4 to which covers 45 and 46 are attached at the upper end and lower end, respectively. The aforementioned drive shaft 30 is also supported by the frame 43, and is connected to motor 42 through cam block C. In the figures, 47 is a waterproofing rubber seal for waterproofing the end of the housing 4, and 48 is bearings which bear the drive shaft 30. The aforementioned cam block C receives a rotary motion from motor 42 and causes the drive shaft 30 to move in a reciprocating rectilinear fashion in the direction of its axis and in a, reciprocating fashion about its axis. This area will be described later.

A switch 8, arranged on a front surface of the housing 4, is formed with two push-on switches 81 and 82, and a push-off switch 83, a switch lever 84, which moves in a seesaw fashion with the operation of the above switches, contacts (not shown) that open and close in tandem with the movement of the switch lever 84, and a switch plate 85. A rotation of the aforementioned motor 42 commences in different directions depending upon whether the push-on switch 81 or push-on switch 82 is pressed.

Figure 3:
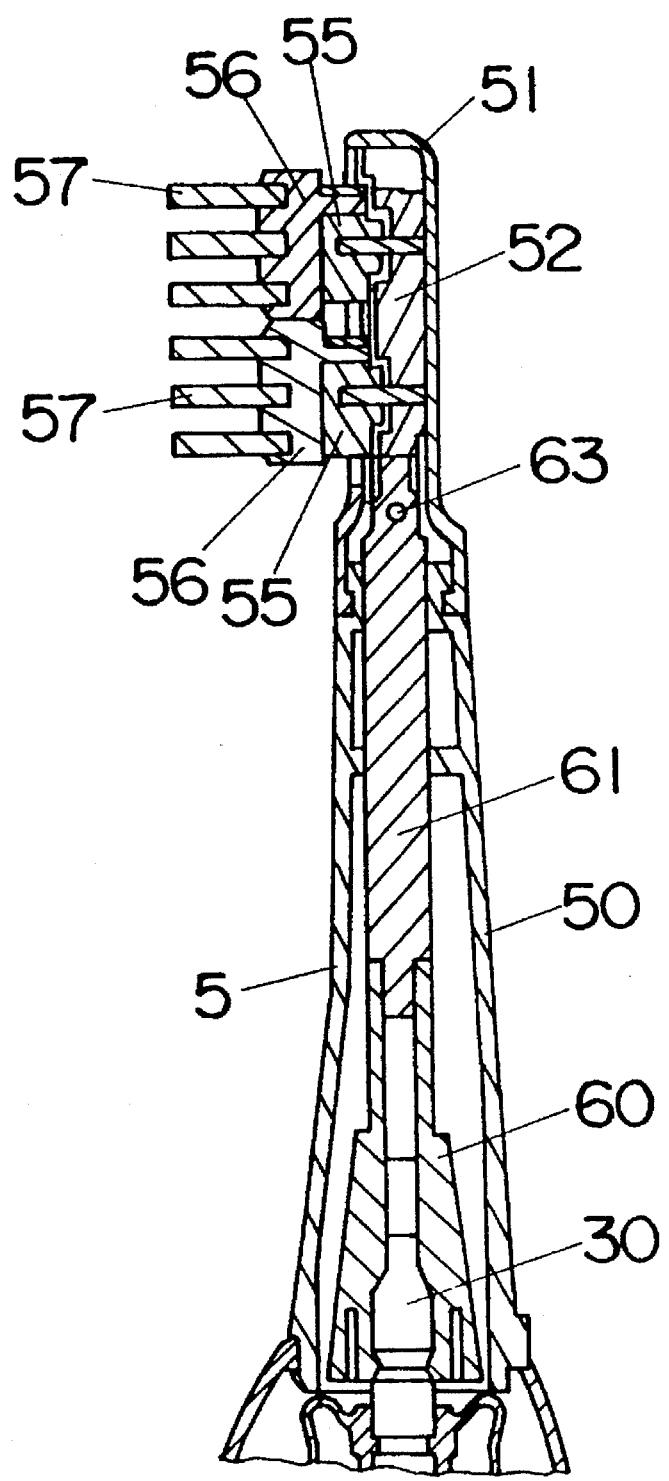
FIG. 3 is a cross-sectional diagram of a toothbrush attachment.
Figure 4:
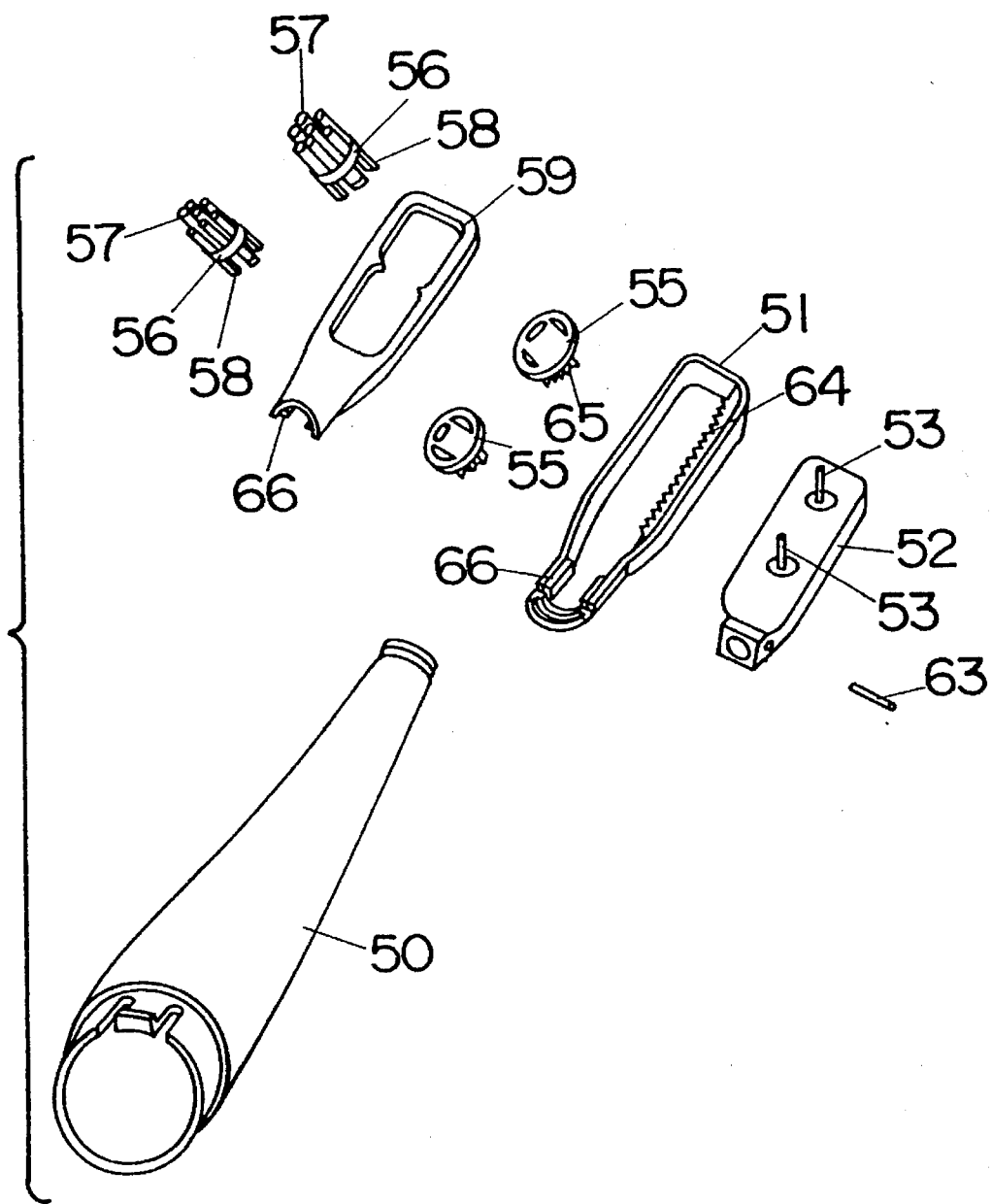
FIG. 4 is a perspective exploded view of a toothbrush attachment.
Figure 5A:
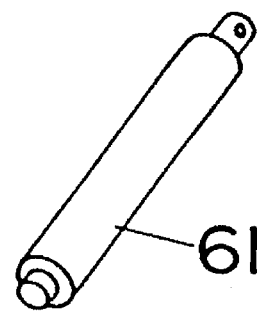
FIG. 5(a) is an oblique exploded view of connecting rods housed within a handle.
Figure 5A:
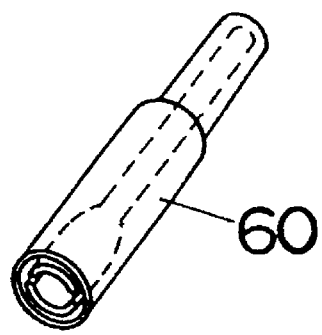
Figure 5B:
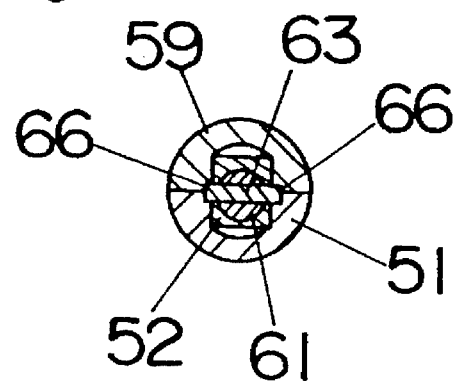
FIG. 5(b) is a cross-sectional diagram of the toothbrush attachment.

Next, as shown in FIGS. 3 to 5, the toothbrush attachment 5 is of a hollow construction and comprises a handle 50, the base of which is removably linked to the cover 45 of the housing 4, a holder 51 attached to the end of the handle 50 such that it is free to rotate about the handle axis, a slider 52 housed within the holder 51 so as to slide freely in the longitudinal direction of the handle 50, circular rotating bases 55 rotatably supported by pins 53 projecting from the slider 52, circular brush bases 56 to one side of which are mounted a plurality of brush bundles 57 and on the other side of which protrude hooks 58 that engage with the rotating bases 55, a cover 59 mounted to an opening in a front surface of the holder 51, and connecting rods 60 and 61 shown in FIG. 5(a) and arranged within the aforementioned handle 50. One end of the drive shaft 30 protruding from the housing 4 is removably connected to one end of the connecting rod 60, and the other end of the connecting rod 60 is press-fitted into one end of the connecting rod 61. The other end of the connecting rod 61 is connected to the aforementioned slider 52 by means of a pin 63.

Thus, the rotating bases 55 which are pivotally supported by means of the pins 53 of the slider 52 are equipped with pinions 65 which mesh with a rack 64 formed on an inner surface of the holder 51. When the slider 52 slides back and forth in the longitudinal direction of the handle 50 within holder 51, the rotating bases 55 and brush bases 56 attached to the rotating bases 55 move in a reciprocating fashion about the axes of the pins 53, in other words, about axes in the direction of projection of the brush bundles 57. Moreover, during the sliding action of slider 52, both ends of the pin 63 passing through the slider 52 and the connecting rod 61 are guided by flats 66 formed on surfaces opposing the holder 51 and cover 59.

Figure 6:
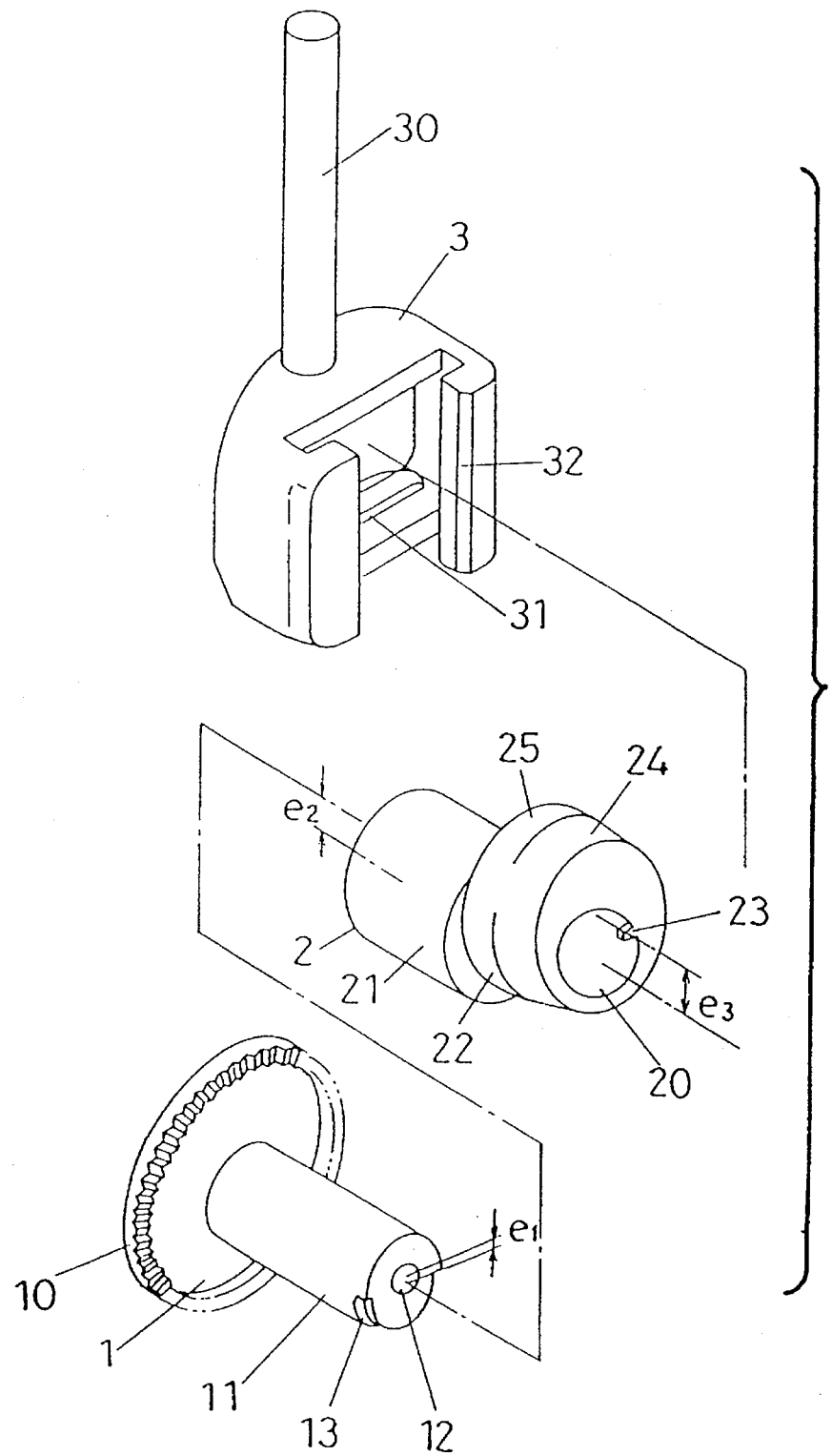
FIG. 6 is a perspective exploded view of a cam block.

Next, the aforementioned cam block C in the housing 4 is explained. This cam block C receives a rotary motion from the motor 42 and causes the drive shaft 30 to move in a reciprocating rectilinear fashion in the direction of its axis and to move in a reciprocating fashion about the axis. As shown in FIG. 6, the cam block C comprises three members: a rotator 1, a cam 2 and cam follower 3. The rotator 1 is formed with a shaft 11 and a face gear 10, and is equipped with a shaft hole 12, through which a shaft 40 passes. In contrast to the fact that face gear 10, which meshes with a pinion 49 attached to an output shaft of the motor 42, is concentric with this shaft hole 12, the shaft 11 is eccentric by just the amount $e_1$ shown in the figure. In addition, an engagement groove 13 is cut into an outer rim at one end of the shaft 11 for a distance of substantially half the circumference.

The cam 2 is equipped with a through-hole 20 that passes through it, and is formed with a reciprocating cam 21 which is eccentric by just the amount $e_2$ with respect to the through-hole 20, a rotating cam 22 which is eccentric by just the amount $e_3$ with respect to the through-hole 20 but in the opposite direction as the eccentricity of the reciprocating cam 21, and a projection 23 projecting from a rim of an opening at one end of the through-hole 20. In addition, a slope 24 which is inclined from the axis of the shaft hole 12 by just the angle 81, as shown in FIGS. 8(a) and 8(b), and a slope 25 which is inclined from the axis of the shaft hole 12 by just the angle 82 in the opposite direction, as shown in FIGS. 9(a) and 9(b), are formed on the outside circumferential surface of the rotating cam 22.

The cam follower 3 is fastened to the lower end of the aforementioned drive shaft 30. The cam follower 3 is equipped with a first follower 31 which has upper and lower inside rims adapted to contact the outside circumferential surface of the reciprocating cam 21 of the cam 2, and a second follower 32 which has inside surfaces adapted to contact the slope 24 or slope 25 of the rotating cam 22 of the cam 2.

The rotator 1 receives a rotary motion from the motor 42 and revolves around the shaft 40. The shaft 11 of the rotator 1 fits inside the through-hole 20 of the cam 2 such that it can turn freely. In addition, the projection 23 of the cam 2 is placed in the engagement groove 23 formed on the shaft 2. The cam follower 3 is supported by the bearings 48 in such a manner to enable the drive shaft 30 to slide freely in the direction of its axis and to rotate freely about its axis. As described above, the cam follower 3 causes the reciprocating cam 21 to contact the first follower 31 and the rotating cam 22 to contact the second follower 32.

Here, the eccentricity $e_1$ of the shaft 11 of the rotator 1 and the eccentricity $e_2$ of the reciprocating cam 21 of the cam 2 have equal values, but the eccentricity $e_3$ of the rotating cam 22 has a value different from that of the aforementioned $e_1$ and $e_2$. As shown in FIG. 7(a), when the projection 23 of the cam 2 engages one end of substantially semicircular engagement groove 13 in the rotator 1, the eccentricity of the shaft 11 and the eccentricity of the reciprocating cam 21 are in mutually inverse directions. Consequently, eccentricity of the reciprocating cam 21 relative to the shaft 40 becomes zero. That is to say, the reciprocating cam 21 becomes concentric with the shaft 40, while eccentricity of the rotating cam 22 relative to the shaft 40 becomes $e_1-e_3$. In contrast, as shown in FIG. 7(b), when the projection 23 engages the other end of engagement groove 13 in the rotator 1, the eccentricity of the shaft 11 and the eccentricity of the reciprocating cam 21 are in the same direction. Consequently, eccentricity of the reciprocating cam 21 relative to the shaft 40 is $e_1+e_a=2e1$, while eccentricity of the rotating cam 22 relative to the shaft 40 becomes $2e_1-e_3$. Angles of inclination $\theta_1$ and $\theta_2$ of the aforementioned slopes 24 and 25 of the rotating cam 22 correspond to values of the eccentricities $e_1-e_3$ and $2e_1-e_3$.

A rotating direction of the rotator 1 determines which end of the engagement groove 13 is engaged to the projection 23. When the rotator 1 is caused to rotate in a clockwise direction as shown by the arrow in FIG. 7(b), the reciprocating cam 21 becomes eccentric relative to the shaft 40, as shown in FIGS. 9(a) and 9(b). In addition, because the slope 25 of the rotating cam 22 contacts the second follower 32 of the cam follower 3, with the rotation of the cam 2 the cam follower 3 moves in a reciprocating rectilinear fashion in the axial direction of the drive shaft 30 while simultaneously moving in a circumaxial reciprocating fashion over a range corresponding to the inclination angle $\theta_2$ of the slope 25.

This movement of the cam follower 3 is transmitted to the slider 52 through the drive shaft 30 which is contiguous with the cam follower 3 and through the connecting rods 60 and 61. The reciprocating rectilinear motion in the axial direction is converted to a reciprocating sliding action of the slider 52, and by means of a rack and pinion engagement between the rotating bases 55 and holder 51, is also converted to a circumaxial reciprocating motion of the rotating bases 55. The circumaxial reciprocating motion of the cam follower 3 is transmitted directly to become a circumaxial reciprocating motion of the slider 52 and holder 51. The brush bases 56 are attached to the rotating bases 55, and are pivotally supported by means of the pins 53 of the slider 52. Accordingly, the brush bases 56 move as a combination of the reciprocating rectilinear motion in the axial direction of the handle 50 (stroke $S=2(e_1+e_22)$), the reciprocating motion about the axis of the handle 50, and the reciprocating motion about the axes of the pins 53. When the brush bundles 57 move in such fashion, a scrub area increases, and the brush bundles 57 do not get trapped between teeth because the brush bundles 57 do not remain in any one location for a long period of time. Further, excluding a component of the reciprocating motion about the axes of the pins 53, the movement of the brush bundles when viewed from the front of the brush bundles 57, describes the letter "O", as shown in FIG. 10(b).

In this situation, as described above, the holder 51 receives from the drive shaft 30 only reciprocating motion about the axis of the handle 50, while the slider 52 receives both of the reciprocating rectilinear motion in the axial direction of the handle 50 and the circumaxial reciprocating motion. That is to say, since the slider 52 performs only reciprocating rectilinear motion with respect to the holder 51, the reciprocating motion about the axes in the projecting direction of the brush bundles 57 can be easily produced through the use of the rack and pinion, or the like.

When the rotator 1 is caused to rotate in a counterclockwise direction, as shown by the arrow in FIG. 7(a), only rotating cam 22 becomes eccentric relative to the shaft 40, while the reciprocating cam 21 becomes concentric with the shaft 40, as described above. The reciprocating cam 21 performs only simple rotation within the first follower 31 of the cam follower 3. The rotating cam 22 causes the second follower 32 to contact the slope 24. The rotating cam 22 also causes the cam follower 3 to move in a circumaxial reciprocating fashion in accordance with a rotation of the rotating cam 22 over a range corresponding to the inclination angle $\theta_1$ of the slope 24, as shown in FIGS. 8(a) and 8(b). This movement of the cam follower 3 delivers to the brush bundles 57 only reciprocating motion about the axis of the handle 50 for a rolling-brushing.

A range of the reciprocating motion in the latter case for the rolling-brushing is smaller than that of the circumaxial reciprocating motion in the former case which produces a compound motion, in order to prevent damage to the gums during the rolling-brushing. However, it is possible to adopt the same ranges. Further, the former case producing the compound motion includes the rotation of the brush bundles 57 and the reciprocating rectilinear motion in the longitudinal direction of the handle 50. Thus, even if a component of the reciprocating motion about the axis of the handle 50 is large, the brush bundles 57 do not fold back the gums at any one particular location, so that there is no danger to the gums.

Figure 5C:
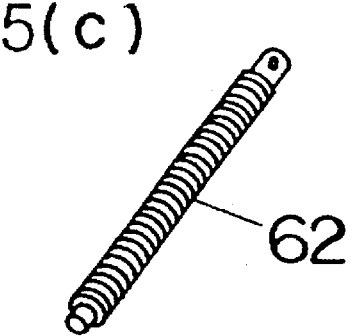
FIG. 5(c) is a perspective view of a connecting spring used in lieu of the connecting rod.

A connecting spring 62 shown in FIG. 5(c) may be used in place of the aforementioned connecting rod 61. In a toothbrush attachment 5 employing this connecting spring 62 in lieu of the connecting rod 61, because the component of reciprocating motion about the axis of the handle 50 is absorbed at the connecting spring 62, only reciprocating rectilinear motion is transmitted to the slider 52. In this case, the brush bundles 57 perform the reciprocating rectilinear motion and the reciprocating motion about the axes of the pins 53. In addition, since previously available regular toothbrush attachments may be used as well, it is possible to implement various brushing actions with the use of the same housing 4.

In another exemplary embodiment shown in FIG. 11, an eccentric portion 15 having the eccentricity $e_5$ is formed at the base of the shaft 11 having the eccentricity $e_1$. The cam 2 is arranged on the outer circumference of the shaft 11, and is provided with the eccentricity $e_2$ which is the same value as the eccentricity $e_1$. The upper and lower inside rims of the first follower 31 of the cam follower 3 contact the eccentric portion 15, while left and right inside rims of the second follower 32 contact the cam 2. When the rotator 1 turns in one direction, eccentricity of the cam 2 relative to the shaft 40 becomes $e_1+e_2$, as shown at FIG. 12(a). As a result, the cam follower 3 describes an orbit of ellipse which is produced by a combination of a vertical reciprocating rectilinear motion having the stroke S (S=2$e_5$) and corresponding to the eccentricity $e_5$ of the eccentric portion 15 contacting to the first follower 31, and a circumaxial reciprocating motion corresponding to the aforementioned eccentricity $e_1+e_2$ of the cam 2 contacting to the second follower 32. As in the above-described embodiment, the brush bundles 57 are made to move, as shown in FIGS. 10(a) and 10(b).

When the rotator 1 turns in the opposite direction, directions of the eccentricities of the cam 2 and shaft 11 mutually oppose and cancel one other, as shown in FIGS. 12(b) and 12(c). Eccentricity of the cam 2 relative to the shaft 40 becomes zero. The cam follower 3 performs only vertical reciprocating rectilinear motion resulting from the eccentricity $e_5$ of the eccentric portion 15. That is, the brush bundles 57 performs a combined movement of the reciprocating rectilinear motion in the axis direction of the handle 50 and the reciprocating motion about the axes of the pins 53.

An exemplary embodiment found in FIG. 13 illustrates a device constructed such that there is no switching operation with respect to a rotating direction of the motor 42. The shaft 11 of the rotator 1 is provided with the eccentric portion 15, and a rotating cam 16 with the same eccentricity. The eccentric portion 15 causes the cam follower 3 and drive shaft 30 to move in the reciprocating rectilinear fashion, while the rotating cam 16 causes the cam follower 3 and drive shaft 30 to move in a reciprocating fashion about the shaft axis. In this device as well, the brush bundles 57 can be made to move as shown in FIGS. 10(a) and 10(b). Moreover, by offsetting directions of the eccentricities of the eccentric portion 15 and rotating cam 16 by 90°, offsetting a phase of the reciprocating rectilinear motion and reciprocating motion about the axis of the handle 50, and setting a dead center of the reciprocating rectilinear motion having stroke S to coincide with the dead center of the reciprocating motion about the axis of handle 50 as shown in FIG. 14(a), a motion of the brush bundles 57, excluding the component of reciprocating motion around the axes of the pins 53, can be made to describe the letter "S" when viewed from the front of the brush bundles 57, as shown in FIG. 14(b).

Further, as shown in FIGS. 15 and 16, when an internal configuration of the second follower 32, which is used to generate a circumaxial reciprocating motion of the cam follower 3, is fashioned in a pattern such as a four-leaf clover, because eccentric components of the rotating cam cancel each other out every 90° and the cam follower 3 can be made to describe two revolutions of the circumaxial reciprocating motion during one rotation of the rotator 1, a motion of brush bundles 57, excluding the component of reciprocating motion around the axes of the pins 53, can be made to describe the numeral "8" when viewed from the front of the brush bundles 57, as shown in FIG. 16(b).

FIG. 17 shows a toothbrush attachment 5 equipped with only one rotatable brush base 56. With this electric toothbrush, regular toothbrush attachments and attachments for cleaning between teeth in prior use may also be used by connecting them to the drive shaft 30.

As described above, according to the invention, a brush moves in a combination of a reciprocating rectilinear motion in the direction of a handle axis, a reciprocating motion about the handle axis, and a reciprocating motion about an axis in the direction of brush projection. The movement is more complex than in a conventional bus-brushing or rolling-brushing and maintains a larger scrub area. Cleaning of the entire tooth surface is possible, and scrubbing of the areas between teeth and gums, the areas between teeth, and the biting surfaces is facilitated. At the same time, by virtue of that movement of the brush, the brush does not become trapped between teeth, and provides effective teeth brushing.

Moreover, if the brush is equipped with a holder that is provided at the end of the handle and that receives only the reciprocating motion about the handle axis produced by a driving device, a slider arranged to slide freely on the holder, which receives both the reciprocating rectilinear motion in the direction of the handle axis and the reciprocating motion about the handle axis produced by the driving device, and a motion converter that produces the reciprocating motion about the axis in the direction of brush projecting from a sliding of the slider relative to the holder, it is possible to obtain the aforementioned three types of movement in a simple, convenient construction.

We claim:

1. An electric toothbrush comprising:

a housing;

a motor located within said housing and having a motor shaft;

a connecting rod extending along an axis of said housing;

a first motion-converting means located within said housing to convert a rotary motion of said motor shaft to a combined motion of a reciprocating rectilinear-motion in an axial direction of said connecting rod and a first reciprocating rotary-motion about the axis of said connecting rod, and to transmit said combined motion to said connecting rod; and a brush head connected to an end of said connecting rod, said brush head being supported to said housing to be rotatable about the axis of said connecting rod for effecting said first reciprocating rotary-motion;

wherein said brush head comprises:

a brush case having an opening;

a slider connected to said end of said connecting rod, said slider being incorporated in said brush case and slidably supported to said brush case to be movable in the axial direction of said connecting rod for effecting said rectilinear-motion;

at least one brush member with bristles projecting outwardly through said opening, said at least one brush member being supported to said slider to be rotatable about a longitudinal axis of said bristles; and a second motion-converting means located between said brush case and said at least one brush member for generating a second reciprocating rotary-motion of said at least one brush member about said longitudinal axis of said bristles from said rectilinear-motion of said slider, to thereby allow said at least one brush member to operate said second reciprocating rotary-motion simultaneously with said combined motion.

2. An electric toothbrush as set forth in claim 1, wherein said first motion-converting means produces said combined motion such that said at least one brush member moves to trace a figure-O pattern.

3. An electric toothbrush as set forth in claim 1, wherein said first motion-converting means produces said combined motion such that said at least one brush member moves to trace a figure-S pattern.

4. An electric toothbrush as set forth in claim 1, wherein said first motion-converting means produces said combined motion such that said at least one brush member moves to trace a figure-eight pattern.

5. An electric toothbrush as set forth in claim 1 further comprising a means for switching between a first mode of producing said combined motion and a second mode of producing only said rectilinear-motion in response to a rotating direction of said motor shaft.

6. An electric toothbrush as set forth in claim 1 further comprising a means for switching between a first mode of producing said combined motion and a second mode of producing only said first reciprocating rotary-motion in response to a rotating direction of said motor shaft.

7. An electric toothbrush as set forth in claim 1, wherein said housing is a handle portion and said brush head is incorporated in a slip-on portion for detachably mounting on said handle portion.

\* \* \* \* \*